United States Patent [19]

Denny, Jr. et al.

[11] 4,314,990
[45] Feb. 9, 1982

[54] TOOTHPASTE COMPOSITIONS

[75] Inventors: William D. Denny, Jr.; Thomas A. Wetzel, both of Cincinnati, Ohio

[73] Assignee: The Procter & Gamble Company, Cincinnati, Ohio

[21] Appl. No.: 84,485

[22] Filed: Oct. 15, 1979

[51] Int. Cl.³ .............................................. A61K 7/18
[52] U.S. Cl. ..................................... 424/52; 424/49; 424/57
[58] Field of Search ..................................... 424/49–58

[56] References Cited

U.S. PATENT DOCUMENTS

| | | | |
|---|---|---|---|
| 3,538,230 | 11/1970 | Pader et al. | 424/50 |
| 3,551,559 | 12/1970 | Miles | 424/49 |
| 3,689,637 | 9/1972 | Pader | 424/52 |
| 3,705,940 | 12/1972 | Kirchgassnor | 424/49 |
| 3,711,604 | 1/1973 | Colodney et al. | 424/52 |
| 3,803,301 | 4/1974 | Cordon et al. | 424/49 |
| 3,836,641 | 9/1974 | Hoyles et al. | 424/49 |
| 3,840,657 | 10/1974 | Norfleet | 424/49 |
| 3,842,167 | 10/1974 | Block et al. | 424/49 |
| 3,864,470 | 2/1975 | Watson | 424/49 |
| 3,893,840 | 7/1975 | Wason | 106/288 B |
| 3,906,090 | 9/1975 | Colodney | 424/52 |
| 3,911,102 | 10/1975 | Harrison | 424/49 |
| 3,911,104 | 10/1975 | Harrison | 424/52 |
| 3,928,541 | 12/1975 | Wason | 423/339 |
| 3,929,987 | 12/1975 | Colodney et al. | 424/52 |
| 3,934,000 | 1/1976 | Barth | 424/49 |
| 3,935,306 | 1/1976 | Roberts et al. | 424/49 |
| 3,939,262 | 2/1976 | Kim | 424/52 |
| 4,141,969 | 2/1979 | Mitchell | 424/52 |
| 4,159,280 | 6/1979 | Wason | 424/52 |

FOREIGN PATENT DOCUMENTS 864872 9/1978 Belgium .
1408922 10/1975 United Kingdom .

*Primary Examiner*—Shep K. Rose
*Attorney, Agent, or Firm*—Richard C. Witte; John V. Gorman; Douglas C. Mohl

[57] ABSTRACT

Fluoride toothpastes which contain a high level of humectant, a silica abrasive and a fluoride ion source and which have a pH of from about 6.8 to about 8.0. Such pastes have superior fluoride and flavor stability.

7 Claims, No Drawings

TOOTHPASTE COMPOSITIONS

TECHNICAL FIELD

This invention relates to novel, high humectant, toothpaste compositions which are exceptionally stable in terms of their ability to provide therapeutic amounts of soluble fluoride for treatment of dental tissue. For purposes of this invention, the "soluble fluoride" content of any given toothpaste composition refers to the ppm concentration of fluoride ion which is found in a supernatant sample centrifuged from a 3:1 by weight slurry of the toothpaste in water (3:1 = water: toothpaste). The improved fluoride stability is important since fluoride ions are believed to interact with dental enamel to reduce the enamel's acid solubility.

It has been postulated that the effectiveness of fluoride toothpastes in providing enamel antisolubility benefits is dependent upon the amount of fluoride ion which is available for uptake by the enamel being treated. It is, of course, therefore desirable to formulate toothpaste products which provide maximum fluoride ion availability in brushing solutions formed therefrom.

Formulation of toothpastes which provide desirable levels of soluble fluoride is not accomplished without certain difficulties. All fluoride toothpastes tend, upon storage, to lose their capability of providing their theoretical maximum amount of soluble fluoride. Fluoride ion sources tend to interact with toothpaste impurities and with such toothpaste components as abrasives, buffers, etc. Such interaction diminishes the ability of the fluoride source to provide "soluble fluoride" upon use.

BACKGROUND ART

Toothpastes containing relatively high levels of humectant, a silica abrasive and a fluoride ion source have been disclosed in the art. Included among the references are U.S. Pat. No. 3,538,230, Nov. 3, 1970 to Pader et al; U.S. Pat. No. 3,689,637, Sept. 5, 1972 to Pader; U.S. Pat. No. 3,711,604, Jan 16, 1973 to Colodney et al; U.S. Pat. No. 3,911,104, Oct. 7, 1975 to Harrison; U.S. Pat. No. 3,935,306, Jan. 27, 1976 to Roberts et al; and U.S. Pat. No. 4,040,858, Aug. 9, 1977 to Wason. Although these references disclose compositions similar to those of the present invention, they do not suggest the necessity and desirability of keeping the pH within a certain narrow range.

Accordingly, it is an object of the present invention to provide toothpaste compositions which contain relatively high levels of humectant, silica dental abrasives, a fluoride ion source, a pH within a certain range and which possess excellent fluoride compatibility.

DISCLOSURE OF THE INVENTION

The present invention relates to toothpaste compositions which exhibit superior fluoride stability. Such compositions comprise a silica abrasive polishing material, a humectant, a fluoride ion source, preferably a buffering agent and water. Such toothpastes provide a pH of from about 6.8 to 8.0 when slurried with water in a 3:1 water/composition weight ratio.

The silica abrasive polishing materials comprise from about 6% to 45% by weight of the composition. Such abrasives can be any silica material having an average particle size of from about 0.1 to 30 microns.

The humectant comprises from about 30% to 70% by weight of the composition.

The fluoride ion source comprises from about 0.1% to 3% by weight of the composition.

The buffering agent comprises an amount sufficient to produce the desired pH, 6.8 to 8.0, preferably 6.9 to 7.3.

The water in the toothpastes herein comprises from about 10% to 45% by weight of the composition

DETAILED DESCRIPTION OF THE INVENTION

The toothpaste compositions of the present invention comprise a silica dental abrasive, a humectant, a fluoride ion source, preferably a buffering agent and water. Each of these components as well as optional ingredients, composition use and composition preparation are described in detail as follows:

SILICA ABRASIVE

The instant toothpaste compositions contain from about 6% to 45%, preferably from about 10% to 30%, by weight of a silica abrasive polishing material. Silica dental abrasives of various types can provide the unique benefits of exceptional dental cleaning and polishing performance without unduly abrading tooth enamel or dentin. Silica abrasive materials are also exceptionally compatible with sources of soluble fluoride.

The silica abrasive polishing material used herein generally has an average particle size ranging between about 0.1 to 30 microns, preferably 5 and 15 microns. The abrasive can be precipitated silica or silica gels such as the silica xerogels described in Pader et al; U.S. Pat. No. 3,538,230; issued Mar. 2, 1970 and incorporated herein by reference. Preferred are the silica xerogels marketed under the tradename "Syloid" by the W. R. Grace & Company, Davison Chemical Division. Especially preferred precipitated silica materials are those marketed by the J. M. Huber Corporation under the tradename, "Zeodent", Particularly the silica carrying the designation "Zeodent 119". The types of silica dental abrasives useful in the toothpastes of the present invention are described in more detail in DiGiulio, U.S. Pat. No. 3,862,307; issued Jan. 21, 1975, incorporated herein by reference.

HUMECTANT

Another essential component of the toothpaste compositions herein is a humectant. The humectant serves to keep the toothpaste compositions from hardening upon exposure to air. Certain humectants can also impart desirable sweetness or flavor to toothpaste compositions. The humectant, on a pure humectant basis, generally comprises from about 30% to 70%, preferably from about 45% to 65%, by weight of the toothpaste compositions herein.

Suitable humectants for use in this invention include edible polyhydric alcohols such as glycerine, sorbitol, xylitol and propylene glycol. Sorbitol is frequently employed as a 70% aqueous solution known as Sorbo ®. Mixtures of glycerine and sorbitol are especially preferred as the humectant component of the toothpaste compositions herein.

FLUORIDE ION SOURCE

The fluoride ion source is present at a level of from about 0.01% to 3%, preferably from about 0.03% to 1.0%, by weight of the instant compositions. Such fluoride ions combine with dental enamel and thereby reduce enamel solubility in acid. Application of fluoride ions to dental enamel serves to protect teeth against decay.

A wide variety of fluoride ion-yielding materials can be employed as sources of soluble fluoride in the instant compositions. Examples of suitable fluoride ion-yielding materials are found in Briner et al; U.S. Pat. No. 3,535,421; issued Oct. 20, 1970 and Widder et al; U.S. Pat. No. 3,678,154; issued July 18, 1972, both patents being incorporated herein by reference. Preferred fluoride ion sources for use herein include sodium fluoride, potassium fluoride and ammonium fluoride. Sodium fluoride is particularly preferred.

Preferably the instant toothpaste compositions provide from about 50 ppm to 10,000 ppm, more preferably from about 100 to 3000 ppm, of fluoride ions in the aqueous solutions which contact dental surfaces when the toothpastes of the present invention are used in the mouth. Such solutions are simulated by preparing 3:1 water/toothpaste slurries (by weight) of the toothpaste compositions herein and by subsequently centrifuging such slurries to obtain an aqueous supernatant. The fluoride ion concentration in such supernatant is taken as a measure of the "soluble fluoride" provided by any given fluoride toothpaste composition.

BUFFERING AGENT

The buffering agents useful in the present compositions are those which are capable of maintaining the desired pH. Systems based on phosphates or tris(hydroxymethyl)aminomethane are two examples of such agents. Preferred agents are the water-soluble phosphate salts. For purposes of this invention a "water-soluble" salt is one which is soluble in water to the extent of at least 3.0 g/100 cc $H_2O$ at 20° C.

The most preferred phosphate salts for use in the present invention are the simple orthophosphate salts. Orthophosphate salts are derived from tribasic orthophosphoric acid of the formula $H_3PO_4$. Water soluble sodium, potassium and ammonium salts can be utilized.

There are about ten different crystalline sodium orthophosphate salts including the various hydrates.

These include, for example, $NaH_2PO_4$, $NaH_2PO_4 \cdot H_2O$, $NaH_2PO_4 \cdot 2H_2O$, $Na_2H PO_4$, $Na_2HPO_4 \cdot 2H_2O$, $Na_2HPO_4 \cdot 7H_2O$, $Na_2HPO_4 \cdot 12 H_2O$, $Na_3PO_4 \cdot 6H_2O$, $Na_3PO_4 \cdot 8H_2O$, and mixtures thereof. Preferred sodium orthophosphates include $NaH_2PO_4 \cdot H_2O$, $Na_2HPO_4 \cdot 2H_2O$, $Na_3PO_4 \cdot 12H_2O$ and mixtures thereof.

Examples of such potassium and ammonium salts which may also be used herein include $KH_2PO_4$, $K_2HPO_4$, $K_2HPO_4 \cdot 2H_2O$, $K_2HPO_4 \cdot 6H_2O$, $K_3PO_4 \cdot 3H_2O$, $K_3PO_4 \cdot 7H_2O$, $K_3PO_4 \cdot 9H_2O$, $(NH_4)H_2PO_4$, $(NH_4)_2HPO_4$, $(NH_4)_3PO_4$ and mixtures of these salts.

An especially preferred phosphate salt mixture for use in the toothpastes herein comprises a mixture of $NaH_2PO_4 \cdot H_2O$ and $Na_3PO_4 \cdot 12H_2O$. Amounts of buffer to supply from about 0.1% to about 1% $PO_4^{-3}$ in the composition are generally required to provide the desired buffer capacity.

The soluble phosphate salts of the present invention are commercially available materials. A more detailed description of such phosphate salts useful herein can be found in Kirk & Othmer, *Encyclopedia of Chemical Technology*, Second Edition, Volume 15, Interscience Publishers, Inc. (1968), pp. 232–276, incorporated herein by reference.

WATER

Water is another essential element of the toothpastes of this invention. Water employed in the preparation of commercially suitable toothpastes should preferably be deionized and free of organic impurities. Water comprises from about 10% to 45%, preferably from about 20% to 35%, by weight of the toothpaste compositions herein. These amounts of water include the free water which is added plus that which is introduced with other materials.

OPTIONAL INGREDIENTS

In addition to the above described essential components, the toothpastes of this invention can contain a variety of optional conventional toothpaste ingredients. Such optional ingredients include binders, sudsing agents, flavoring agents, sweetening agents, anticalculus agents, antiplaque agents, coloring agents and pigments.

A binding agent is preferably present in the present compositions to provide a desirable consistency. Such thickening agents include xanthan gum, hydroxyethyl cellulose and water-soluble salts of cellulose ethers such as carboxyvinyl polymers of the type sold by the B. F. Goodrich Company under the name Carbopol, sodium carboxymethyl cellulose and sodium carboxymethyl hydroxyethyl cellulose. Thickeners of this type are described more fully in Unilever, British Pat. Specification No. 1,372,382, published Oct. 30, 1974; Salzman, U.S. Pat. No. 3,506,757, issued Apr. 14, 1970 and Beecham Group Ltd., Belgian Pat. No. 830,375, published Dec. 18, 1975. All of these patents are incorporated herein by reference. Natural gums such as carrageenan (Irish moss, Viscarin ®), gum karaya, gum arabic, and gum tragacanth can also be used. Colloidal magnesium aluminum silicate, Veegum or finely divided silica can be used as part of the thickening agent system. Preferred thickening agents include carboxyvinyl polymers, xanthan gum, carrageenan, sodium carboxymethyl cellulose, sodium carboxymethyl hydroxyethyl cellulose and hydroxyethyl cellulose. The most preferred thickener is a carboxyvinyl polymer. Thickening agents in an amount from 0.03% to 5.0% by weight of the total composition can be used.

Another preferred optional ingredient is a sudsing agent. Suitable sudsing agents are those which are reasonably stable and form suds throughout a wide pH range, i.e., non-soap anionic, nonionic, cationic, zwitterionic and amphoteric organic synthetic detergents. Sudsing agents of these types are described more fully in Agricola et al; U.S. Pat. No. 3,959,458; issued May 25, 1976 and Haefele; U.S. Pat. No. 3,937,807; issued Feb. 10, 1976. Both of these patents are incorporated herein by reference.

Anionic sudsing agents useful herein include the water-soluble salts of alkyl sulfates having from 10 to 18 carbon atoms in the alkyl radical and the water-soluble salts of sulfonated monoglycerides of fatty acids having from 10 to 18 carbon atoms. Sodium lauryl sulfate and sodium coconut monoglyceride sulfonates are examples of anionic surfactants of this type. Mixtures of anionic surfactants can also be employed.

The nonionic sudsing agents which can be used in the toothpastes of the present invention can be broadly defined as compounds produced by the condensation of alkylene oxide groups (hydrophilic in nature) with an organic hydrophobic compound which may be aliphatic or alkylaromatic in nature. Examples of suitable nonionic sudsing agents include the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials.

The zwitterionic synthetic sudsing agents useful in the toothpastes of the present invention can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate, or phosphonate.

The cationic sudsing agents useful in the toothpastes of the present invention can be broadly defined as quaternary ammonium compounds having one long alkyl chain containing from about 8 to about 18 carbon atoms such as lauryl trimethylammonium chloride; cetyl pyridinium chloride; cetyl trimethylammonium bromide; di-isobutylphenoxyethyl-dimethylbenzylammonium chloride; coconutalkyltrimethylammonium nitrite; cetyl pyridinium fluoride; etc. Especially preferred are the quaternary ammonium fluorides described in U.S. Pat. No. 3,535,421, Briner et al, issued Oct. 20, 1970, incorporated by reference hereinbefore, where said quaternary ammonium fluorides have detergent properties. The cationic sudsing agents can also act as germicides in certain of the toothpastes herein.

The amphoteric sudsing agents useful in the present invention can be broadly described as derivatives of aliphatic secondary and tertiary amines in which the aliphatic radical can be straight chain or branched and wherein one of the aliphatic substituents contains from about 8 to about 18 carbon atoms and one contains an anionic water-solubilizing group, e.g., carboxylate, sulfonate, sulfate, phosphate, or phosphonate.

The sudsing agent can be present in the toothpaste compositions of this invention in an amount from 0.1% to 6% by weight of the total composition.

Flavoring agents can also be added to the instant compositions. Suitable flavoring agents include oil of wintergreen, oil of peppermint, oil of spearmint, oil of sassafras, and oil of clove. Sweetening agents which can be used include saccharin, dextrose, levulose, aspartame, D-tryptophan, dihydrochalcones and sodium cyclamate. Flavoring agents are generally used in toothpastes at levels of from about 0.01% to 2% by weight and sweetening agents at levels of from about 0.05% to about 2% by weight.

When wintergreen flavors are used it has been found that a pH within the range of 6.9 to 7.3 maximizes both fluoride and flavor stability.

Phosphorus-containing anticalculus agents and/or bis-biguanide antiplaque agents can also optionally be added to the toothpastes of this invention. Phosphorus-containing anticalculus agents such as disodium ethane-1-hydroxy-1, 1-diphosphonate and related materials are described more fully in McCune et al; U.S. Pat. No. 3,488,419, issued Jan. 6, 1970, incorporated herein by reference. Bis-biguanide antiplaque agents such as chlorhexidine (1,6-bis[$N^5$-p-chlorophenyl-n$^1$-biguanido]hexane), the soluble and insoluble salts thereof and related materials such as 1,2-bis($N^5$-p-trifluoromethylphenyl-$N^1$-biguanido)ethane are described more fully in Haefele, U.S. Pat. No. 3,934,002, issued Jan. 20, 1976; Haefele, U.S. Pat. No. 3,937,807, issued Feb. 10, 1976; Procter & Gamble, Belgian Pat. No. 843,244, published Dec. 22, 1976 and Procter & Gamble, Belgian Pat. No. 844,764, published Jan. 31, 1977. These patents are incorporated herein by reference.

If present, the optional anticalculus and/or antiplaque agents generally comprise from about 0.01% to 2.5% by weight of the toothpaste compositions herein.

METHOD OF MANUFACTURE

Toothpaste compositions of the present invention are prepared simply by mixing together in any order and by any conventional means the essential and optional components herein. Once prepared, the compositions herein provide a pH of from about 6.8 to 8.0, preferably 6.9 to 7.3., when said compositions are slurried with water in a 3:1 weight ratio of water to composition. Fluoride toothpastes providing pH values within the 6.8 to 8.0 range provide especially effective dental enamel antisolubility benefits compared to toothpastes with pH values outside this range. Flavoring of toothpastes within this pH range is also comparatively easy.

Toothpastes which provide slurries having pH values within the 6.8 to 8.0 range are especially suitable for soluble fluoride stabilization.

COMPOSITION USE

Toothpaste compositions of the present invention are used in conventional manner. The toothpaste compositions or slurries are brushed onto dental surfaces and subsequently rinsed away.

During use of the toothpaste herein in conventional manner, pastes or slurries generally contact dental surfaces for at least about 30 seconds. More preferably such pastes or slurries contact dental surfaces for at least about 60 seconds.

Several representative toothpastes of the present invention are set forth in the following examples. All percentages used herein are by weight unless otherwise designated.

EXAMPLE I

A toothpaste of the present invention having the following composition is formulated:

| | |
|---|---|
| Sorbitol (70% Aqueous) | 58.760 |
| Glycerine | 15.000 |
| $NaH_2PO_4 \cdot H_2O$ | 0.025 |
| $Na_2HPO_4 \cdot 2H_2O$ | 0.225 |
| Sodium Saccharin | 0.250 |
| Syloid 63* | 3.000 |
| Syloid 74* | 13.000 |
| Flavor | 0.920 |
| Water | 4.061 |
| Sodium Fluoride | 0.243 |
| Carbopol 940** | 0.250 |
| Xanthan Gum | 0.200 |
| Sodium Alkyl ($C_{12}$) Sulfate (28.8% Aqueous) | 4.000 |
| Color (1% Aqueous) | 0.066 |
| | 100.000 |

*Xerogel silica abrasives - W. R. Grace & Company, Davison Chemical Division
**Carboxyvinyl polymer - B. F. Goodrich Company.

EXAMPLE II

Another toothpaste of the present invention having the following formula is formulated.

| | |
|---|---|
| Sorbitol (70% Aqueous) | 51.002 |
| Sodium Saccharin | 0.220 |
| Trisodium Phosphate | 1.100 |
| Titanium Dioxide | 0.600 |
| Water | 3.000 |
| Flavor | 1.060 |
| Precipitated Silica* | 20.000 |
| Glycerine | 18.000 |
| Carbopol 940 | 0.250 |
| Xanthan Gum | 0.500 |
| Sodium Alkyl ($C_{12}$) Sulfate (28.8% Aqueous) | 4.000 |
| Sodium Fluoride | 0.243 |
| Color | 0.025 |
| | 100.00 |

*Supplied by J. M. Huber Corporation having the designation Zeodent 119.

EXAMPLE III

A third toothpaste of the present invention having the following formula is formulated.

| | |
|---|---|
| Sorbitol (70% Aqueous) | 50.197 |
| Sodium Saccharin | 0.120 |
| $Na_3PO_4 \cdot 12H_2O$ | 1.450 |
| $NaH_2PO_4 \cdot H_2O$ | 0.590 |
| Titanium Dioxide | 0.700 |
| Precipitated Silica* | 20.000 |
| Water | 3.000 |
| Sodium Fluoride | 0.243 |
| Glycerine | 18.000 |
| Carbopol 940 | 0.250 |
| Xanthan Gum | 0.500 |
| Flavor | 0.900 |
| Sodium Alkyl ($C_{12}$) Sulfate (28.8% Aqueous) | 4.000 |
| Color (1% Aqueous) | 0.050 |
| | 100.00 |

*As in Example II.

What is claimed is:

1. A toothpaste composition comprising:
   (A) from about 6% to 45% of a silica dental abrasive;
   (B) from about 30% to 70% of a humectant;
   (C) from about 0.01% to 3% of a fluoride ion source; and
   (D) from about 10% to 45% of water; said composition additionally containing an amount of a phosphate buffering agent providing from about 0.1% to 1% $PO_4^{-3}$, the amount being sufficient to maintain the pH of a 3:1 water/composition weight ratio slurry in the range of about 6.8 to 8.0.

2. A toothpaste composition in accordance with claim 1 wherein the amount of silica dental abrasive is from about 10% to 30% and the amount of humectant is from about 45% to 65%.

3. A toothpaste composition in accordance with claim 2 wherein the fluoride ion source is sodium fluoride.

4. A toothpaste composition in accordance with claim 3 which contains an additional toothpaste composition component selected from the group consisting of
   (A) from about 0.1% to 6% of a sudsing agent;
   (B) from about 0.01% to 2% of a flavoring agent;
   (C) from about 0.05% to 2% of a sweetening agent;
   (D) from about 0.03% to 5% of a toothpaste binder; and
   (E) mixtures of these additional toothpaste composition components.

5. A toothpaste composition in accordance with claim 4 wherein:
   (A) the sudsing agent is selected from the group consisting of water-soluble alkyl sulfates, water-soluble salts of sulfonated monoglycerides and mixtures thereof;
   (B) the humectant is selected from the group consisting of glycerine, sorbitol, xylitol and mixtures thereof; and
   (C) the silica abrasive is a precipitated silica.

6. A toothpaste composition in accordance with claim 5 wherein the amount of buffering agent is sufficient to maintain the pH in the range of about 6.9 to 7.3.

7. A toothpaste composition in accordance with claim 6 which in addition contains a flavoring agent containing methyl salicylate.

* * * * *

REEXAMINATION CERTIFICATE (1545th)

United States Patent [19]

Denny, Jr. et al.

[11] B1 4,314,990

[45] Certificate Issued Sep. 3, 1991

[54] TOOTHPASTE COMPOSITION

[75] Inventors: William D. Denny, Jr.; Thomas A. Wetzel, both of Cincinnati, Ohio

[73] Assignee: The Proctor & Gamble Co., Cincinnati, Ohio

Reexamination Request:
No. 90/001,945, Feb. 27, 1990

Reexamination Certificate for:
Patent No.: 4,314,990
Issued: Feb. 9, 1982
Appl. No.: 84,485
Filed: Oct. 15, 1979

[51] Int. Cl.$^5$ ............................................. A61K 7/18

[52] U.S. Cl. .................................... 424/52; 424/49; 424/57

[58] Field of Search ................................. 424/52, 57

[56] References Cited

U.S. PATENT DOCUMENTS 4,203,966  5/1980  Faunce .................. 424/52

FOREIGN PATENT DOCUMENTS 862384  12/1977  Belgium .

Primary Examiner—Shep K. Rose

[57] ABSTRACT

Fluoride toothpastes which contain a high level of humectant, a silica abrasive and a fluoride ion source and which have a pH of from about 6.8 to about 8.0. Such pastes have superior fluoride and flavor stability.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1 to 7 is confirmed.

* * * * *